United States Patent
Scholten et al.

(10) Patent No.: US 8,839,828 B2
(45) Date of Patent: Sep. 23, 2014

(54) FILLING DEVICE HAVING COOLING AND SYSTEM FOR ADMINISTERING A LIQUID MEDICATION

(75) Inventors: Dick Scholten, Stuttgart (DE); Michael Stumber, Korntal-Muenchingen (DE)

(73) Assignee: Robert Bosch GmbH, Stuttgart (DE)

( * ) Notice: Subject to any disclaimer, the term of this patent is extended or adjusted under 35 U.S.C. 154(b) by 1126 days.

(21) Appl. No.: 12/734,466

(22) PCT Filed: Nov. 17, 2008

(86) PCT No.: PCT/EP2008/065664
§ 371 (c)(1),
(2), (4) Date: Sep. 24, 2010

(87) PCT Pub. No.: WO2009/065801
PCT Pub. Date: May 28, 2009

(65) Prior Publication Data
US 2011/0023997 A1 Feb. 3, 2011

(30) Foreign Application Priority Data
Nov. 21, 2007 (DE) .......................... 10 2007 055 635

(51) Int. Cl.
| | | |
|---|---|---|
| B65B 1/04 | (2006.01) | |
| A61M 5/44 | (2006.01) | |
| A61M 5/20 | (2006.01) | |
| A61M 5/00 | (2006.01) | |
| A61M 5/178 | (2006.01) | |
| A61M 5/142 | (2006.01) | |

(52) U.S. Cl.
CPC ................. *A61M 5/44* (2013.01); *A61M 5/204* (2013.01); *A61M 2205/3606* (2013.01); *A61M 2209/045* (2013.01); *A61M 2209/086* (2013.01); *A61M 5/001* (2013.01); *A61M 5/1782* (2013.01); *A61M 2205/123* (2013.01); *A61M 2005/14268* (2013.01)
USPC .................. 141/25; 141/21; 141/198; 141/82; 141/330; 604/191

(58) Field of Classification Search
USPC ............. 141/18, 21, 25, 26, 28, 82, 104, 105, 141/198, 330; 604/191
See application file for complete search history.

(56) References Cited

U.S. PATENT DOCUMENTS

| | | | |
|---|---|---|---|
| 3,714,943 A | | 2/1973 | Yanof et al. |
| 5,329,976 A | * | 7/1994 | Haber et al. .................... 141/25 |
| 5,697,407 A | * | 12/1997 | Lasonde ..................... 141/104 |
| 5,938,640 A | | 8/1999 | Maget et al. |
| 7,398,802 B2 | * | 7/2008 | Baker ............................ 141/27 |

(Continued)

FOREIGN PATENT DOCUMENTS

| | | |
|---|---|---|
| DE | 103 52 456 | 7/2005 |
| DE | 102004035061 | 2/2006 |

(Continued)

*Primary Examiner* — Jason K Niesz
(74) *Attorney, Agent, or Firm* — Kenyon & Kenyon LLP

(57) ABSTRACT

A system having a medication reservoir for a medication dosing apparatus for administering a liquid medication, and having a medication supply container holding the liquid medication, a filling device being provided for the automatic filling of the medication reservoir with the medication coming from the medication supply container. Fluidic connections may be provided between individual components for transfer and filling of the liquid medication. This system for administering a medication has the advantage that reliable and simple filling of the medication may be performed.

17 Claims, 2 Drawing Sheets

(56) References Cited

U.S. PATENT DOCUMENTS

| | | | |
|---|---|---|---|
| 8,434,528 B2 * | 5/2013 | Ibranyan et al. | 141/18 |
| 2007/0106218 A1 | 5/2007 | Yodfat et al. | |
| 2007/0135765 A1 | 6/2007 | Miller et al. | |

FOREIGN PATENT DOCUMENTS

| | | |
|---|---|---|
| EP | 1170024 | 1/2002 |
| EP | 1 757 320 | 2/2007 |
| WO | 2007/092637 | 8/2007 |

* cited by examiner

FILLING DEVICE HAVING COOLING AND SYSTEM FOR ADMINISTERING A LIQUID MEDICATION

FIELD OF THE INVENTION

The present invention relates to a system having a medication reservoir for a medication dosing apparatus for administering a liquid medication, and having a medication supply container holding the liquid medication.

BACKGROUND INFORMATION

Systems for administering a liquid medication have great importance in various fields of application, such as in medicinal technology, and are used, for instance, to administer insulin, using a medication dosing apparatus in the case of a diabetic patient.

Various systems for administering a liquid medication, especially insulin, are known from the related art. Most of these systems for continuous insulin administration use insulin pumps, which supply an individual daily profile of insulin to the body from a reservoir. Requirements for sterility limit the usability as well as the volume of the reservoir, as well as all the components that are in contact with the medication to about three days.

A system for administering liquid medications, especially insulin, is discussed in DE 103 52 456 A1, which has a medication reservoir developed to have a pumping device and a supply line connected to the body of the patient. According to this design, the pumping device and the medication reservoir are developed in common in one component, the medication reservoir being able to be designed so as to be exchangeable. This design, as well as others known from the related art, have the disadvantage that filling the medication reservoir with insulin requires manual work and is not simple. The filling particularly has to be free of bubbles. Furthermore, storing insulin is permitted only in glass containers and at a cool temperature. This makes the production of reservoirs that are already filled by the manufacturer dependent on an uncertain method subject to registration.

SUMMARY OF THE INVENTION

By contrast, the system according to the exemplary embodiments and/or exemplary methods of the present invention for administering a medication has the advantage that reliable and simple filling of the medication may be performed.

An object according to the exemplary embodiments and/or exemplary methods of the present invention is attained by a system having a medication reservoir for a medication dosing apparatus for administering a liquid medication, and having a medication supply container, wherein, in addition, a filling device is provided for the automatic filling of the medication reservoir with the medication from the medication supply container.

According to the exemplary embodiments and/or exemplary methods of the present invention, this provides a filling device that enables an automatic filling of the medication reservoir with medication from the medication supply container. This makes the filling substantially simpler, and reliable operation is ensured. In particular, no special instruction is required for operating the filling device.

The filling of the medication reservoir is able to be carried out as described below: The operator, for instance, especially the patient himself, a nurse or a doctor, takes the medication reservoir out of the medication dosing apparatus and inserts the medication reservoir into the filling device. The filling device produces fluidic contact between the medication supply container and the medication reservoir. It is provided in particular that the filling of the medication reservoir with the medication should start automatically. The filling may end again automatically after a predetermined quantity, or the filling is stopped by an operator after a certain quantity. Thereafter, the operator takes the medication reservoir out of the filling device and inserts the medication reservoir into the medication dosing apparatus.

One refinement of the exemplary embodiments and/or exemplary methods of the present invention is that the medication reservoir is provided as a unit that is able to be inserted into the medication dosing apparatus and removed again from the medication dosing apparatus. It is particularly provided that the removable unit is able to be inserted into the filling device and removed again. The removable unit is basically able to be inserted, using simple handling, on the one hand, into the filling device and, on the other hand, into the medication dosing apparatus. In order to simplify the insertion, a guideway and/or an engaging mechanism is provided, according to one refinement. The medication reservoir may be feasible, for example, as a cartridge or a bag.

Moreover, an administration needle and a medication dosing device may be provided in the removable unit. The medication supply container, the medication dosing device and the administration needle have fluidic connections between the individual components. The medication dosing device conveys the medication and injects it into the patient via the administration needle.

According to the exemplary embodiments and/or exemplary methods of the present invention, this creates a subdivision between the component that is in direct contact with the medication and the patient, on the one hand, and the additional components on the other hand. In this way, a cost-saving reuse of the additional components, that are separate from the components situated in the removable unit, is achieved. At the same time, the components that have to be compliant with the sterility requirements, are situated together in the removable unit, and are thus easily exchangeable.

In the positioning of the reservoir, the dosing device and the administration needle in the removable unit, the removable unit may be configured as a disposable item. In the delivery state, the disposable item may be packaged to be sterile, in order to live up to the sterility requirements. For the filling with a medication, the disposable item is taken from its sterile packaging, is inserted into the filling device and the filling process is started. After being used in the medication dosing apparatus, the disposable item is exchanged as soon as the medication in the reservoir is used up or has expired or decayed. When handled properly, the disposable item has better sterile properties than reusable reservoirs, medication dosing devices and administration needles. Possible mass production makes it cost-effective to prepare. Furthermore, even parts of the filling device, which have come into contact with the medication, may be exchangeable.

The filling device may basically be operable in a manual manner. According to one refinement of the present invention, it is provided however that the filling device be operable electrically, especially for the automatic refilling of the medication reservoir. This results in increased convenience for the user. The filling device, for instance, driven by an electric motor or an electric control, positions the medication reservoir after its introduction into the filling device, and, driven electrically, produces the fluidic contact between the medication reservoir and the medication supply container. The filling takes place using an electrical unit. After the filling has taken place, the filling device, again driven, for example, by an electric motor or an electrical control, breaks the fluidic connection between the medication reservoir and the medication supply container. According to one further development, the motor or the electrical control disengages the medication reservoir, for example, from an engaging mechanism, and thereby simplifies its removal from the filling device.

The medication supply container may basically be inserted into the filling device before each filling and be removed after the filling. This may be conditioned on the fact that medications, such as particularly insulin, have to be stored in cooled fashion. According to another refinement of the present invention, it is provided, however, that the filling device have a cooling device for the medication supply container. The medication supply, container is able to remain in the filling device because of the cooling device. This eliminates the dependence upon external cooling, such as by a refrigerator. The refinement according to the exemplary embodiments and/or exemplary methods of the present invention simplifies the applicability of the filling device.

Another refinement of the present invention is that the filling device has a purification device. This makes possible, for example, a sterile cleansing of the medication reservoir, of the removable unit and/or the disposable item as well as of the cleansing device before the filling with medication. One may clean the filling device before and/or after the filling. The filling device is able to signal when the medication supply container and/or the medication reservoir have been removed from the filling device, so that the cleansing may begin.

Moreover, the cleansing device may have a cleansing agent. The cleansing agent, for instance, an isotonic table salt solution or an alcoholic solution, makes possible the sterile cleansing of the cleansing device as well as all the components that are in touch with the medication. This basically makes possible the reuse of all the components that are in touch with the medication, or at least a multiple utilization of these components. The reuse reduces the operating costs. According to one refinement, the cleansing agent is provided in a container or a supply tank in the cleansing device. At the beginning of a cleansing process, a predetermined quantity of cleansing agent flows into the cleansing device. It may also be provided that the cleansing agent is already contained in the disposable item that is removed from sterile packaging.

A liquid level monitoring for the medication reservoir may be provided in the filling device. When the medication reservoir is inserted, before the filling process, the liquid level monitoring checks whether the medication reservoir is empty. During the filling process, the liquid level monitoring checks the progress of the filling process. When a sufficient quantity is present in the medication reservoir, the liquid level monitoring stops the filling process, for instance by signaling to an electrical control or the output of an acoustical or visual signal that is recognizable to the operator. It is also provided that the liquid level monitoring is able to represent the charge on a display. The liquid level monitoring may basically also check the liquid level of the medication supply container. The liquid level monitoring signals the falling below a certain quantity, so that the operator or the patient is informed that a new medication supply is needed.

The filling device may have a device for functional checking and/or calibration of the removable unit. In the continuous dispensation of a medication, especially of insulin, it is important that the dispensing be very reliable and given in exactly the quantities and the timely dosage that are required for the medication and the state of health of the patient, and that has been ordered by the doctor. The functional checking checks the removable unit before filling with the medication, for instance, for tightness of the medication reservoir, the functionality of the medication dosing device, and the quantity conveyed per unit of time. Possible deviations, for instance, too high a quantity conveyed per unit of time, may be compensated for by the calibration device, Other shortcomings, which the calibration itself cannot remove, such as a leaking medication reservoir, is reported to the operator by the calibration device, for example, by an acoustical or visual signal. Furthermore, the functional checking checks the general state of the filling device, and reports, for example, pending maintenance or a required overhaul of the filling device. Moreover, it may be provided that the removable unit is outfitted with sensors or sensor elements, for example, for measuring temperature, pressure and/or for flow measurement which, when the removable unit is inserted into the filling device, are connected to the filling device.

According to one refinement, the filling device has a detecting device for an automatic detection of the medication supply container and/or an automatic detection of the shelf life of the medication coming from the medication supply container. In this context, the detection of the medication as well as of the shelf life of the medication may be performed in different ways. According to one further development of the present invention, it may be provided, however, that the medication supply container is provided with a barcode, a ticket or an RFID, which is recognized by the filling device via a reading device or a scanner. The filling process begins, provided criteria such as correct medication and sufficient shelf life are satisfied. If the criteria are not satisfied, an acoustical or visual signal, for example, signals that the filling process cannot start automatically, and that the operator has to intervene.

Furthermore, the administration needle may have a fluidic connection to the medication supply container when the removable unit is inserted into the filling device. In this way, the filling of the medication reservoir takes place via the administration needle that is fluidically connected to the medication supply container which, on its part, has a fluidic connection to the medication dosing device, which has a fludic connection to the medication reservoir. Moreover, the filling may take place by the medication dosing device conveying the medication from the medication supply container into the medication reservoir. That being the case, the medication dosing device fulfills a double function: For one, the conveying of the medication from the medication reservoir via the administration needle to the injection location, and secondly, the filling of the medication reservoir in the filling device. It may further be provided that the administration needle is only exposed when the removable unit is inserted into the filling device.

According to one improvement, the medication supply container has an additional fluidic connection to the removable unit. In particular, it is provided that the medication supply container have a fluidic connection to the medication reservoir. In addition, a fluidic connection may be provided between the medication supply container and the drive for conveying the medication, the medication dosing device, during the filling, having such a passage location that the medication is able to flow from the medication supply container into the medication reservoir. It may also be provided that the medication dosing device conveys the medication from the medication supply container into the medication reservoir.

The filling device may be furnished with a pump for the automatic filling of the medication reservoir, which may have a fluidic connection to the administration needle or the medication reservoir. The pump pumps the medication from the medication supply container into the medication reservoir. Various embodiments are possible, in this context.

In a first embodiment, the pump is in fluidic connection to the administration needle, while the medication supply container is in fluidic connection to the medication reservoir. To aspirate the medication, the pump generates an underpressure, so that the medication reaches the medication reservoir from the medication supply container. In a further embodiment, the pump is in fluidic connection to the medication reservoir, while the administration needle is in fluidic connection to the medication supply container. In further embodiments, the medication supply container is in fluidic connection to the pump, and is, in turn, in fluidic connection to the medication reservoir.

In yet another refinement of the exemplary embodiments and/or exemplary methods of the present invention, the administration needle is one or a plurality of microneedles. Compared to the usual administration needles, microneedles have the advantage that the diameter is smaller by at least a factor of five and they are usually shorter.

One further development of the exemplary embodiments and/or exemplary methods of the present invention provides that the medication dosing device is a micropump, which, among other things, may be produced by using micropatterning methods of Si microsystems technology. The drive of the micropump is a part of the medication dosing apparatus, but does not have to be included in the removable unit.

The filling device described above may have applications in medical technology, for instance, in the insulin filling addressed above, and also in analgesics or psychopharmaceuticals for continuous administration using medication dosing apparati.

Exemplary embodiments of the present invention are described in detail below, with reference to the accompanying drawings.

DETAILED DESCRIPTION

Figure 1:
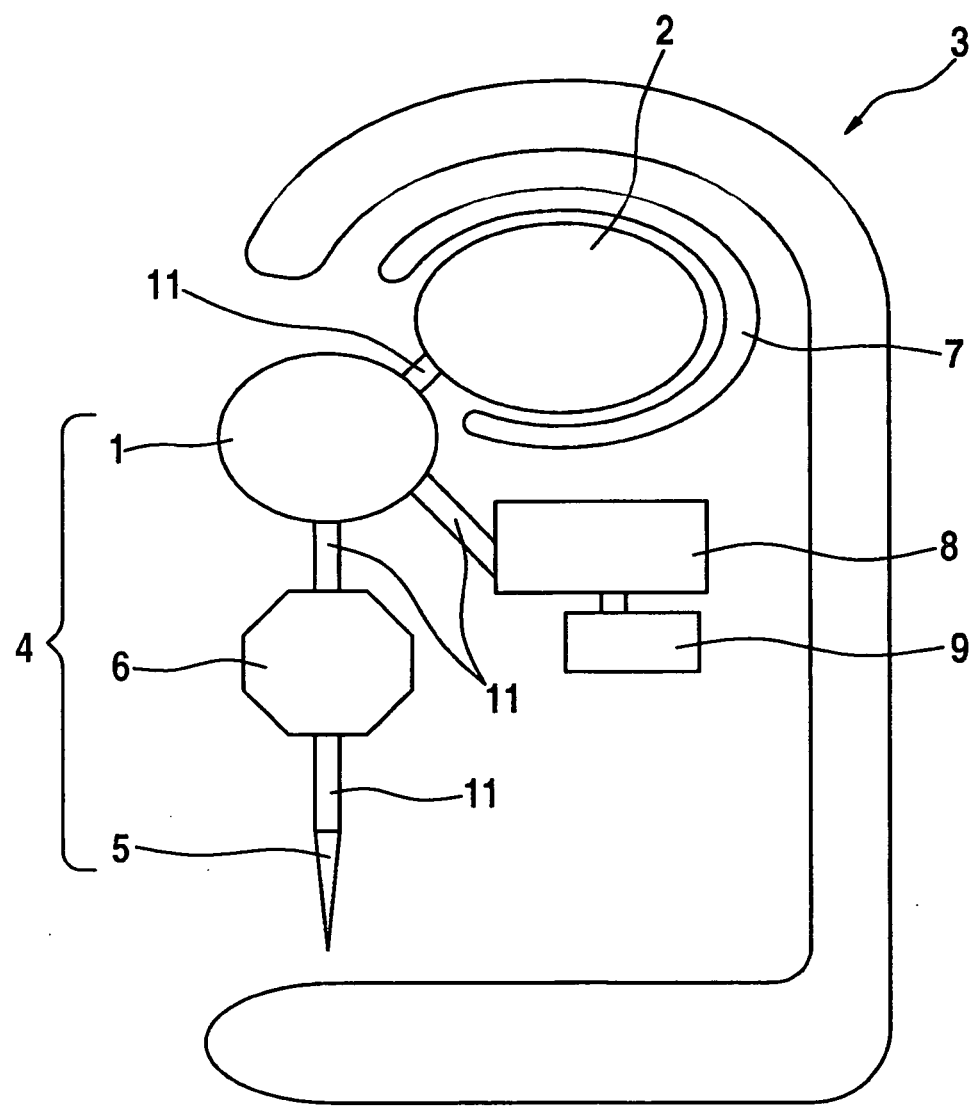
FIG. 1 shows a schematic representation of a filling device according to a first exemplary embodiment of the present invention, showing its essential functioning blocks.
Figure 2:
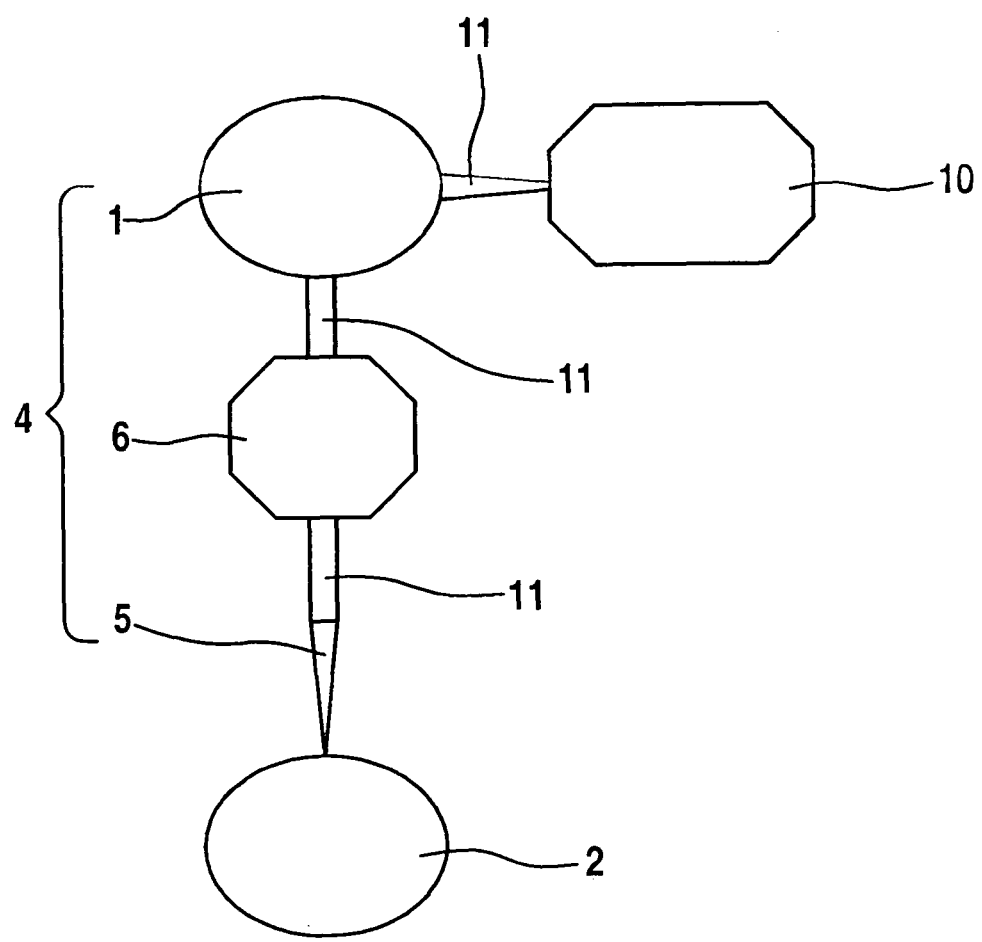
FIG. 2 shows a schematic representation of a filling device according to a second exemplary embodiment of the present invention.

One may see in each of FIGS. 1 and 2 a schematic representation of a filling device 3 according to a exemplary embodiment of the present invention. These filling devices 3 are used for filling a medication dosing apparatus and they each have a medication reservoir 1, a medication dosing device 6 and an administration needle 5, as shown, for instance, in FIG. 1.

Medication reservoir 1, medication dosing device 6 and administration needle 5 have fluidic connections 11 to one another. Medication reservoir 1 is connected to medication dosing device 6, via a first fluidic connection 11, and it is connected to administration needle 5 via a further fluidic connection 11. A medication, filled into medication reservoir 1, is injected into a patient via administration needle 5, using medication dosing device 6.

As may be seen in FIG. 1, medication reservoir 1, medication dosing device 6 and administration needle 5 are provided in common in a unit 4 that is insertable into the medication dosing apparatus as well as into filling device 3 and that is removable from them again. Removable unit 4 is shown inserted into filling device 3, in FIG. 1.

Filling device 3 has a medication supply container 2, cooled by a cooling device 7, a cleansing device 8 as well as a cleansing agent 9. As may be seen in FIG. 1, medication supply container 2 has a fluidic connection 11 to medication reservoir 1. Cleansing device 8 also has a fluidic connection to removable unit 4.

According to a second specific embodiment, shown in FIG. 2, medication supply container 2 has a fluidic connection 11 to administration needle 5, and a pump 10 has a fluidic connection 11 to medication reservoir 1. Except for that, the design of the second specific embodiment, shown in FIG. 2, is the same as that of first specific embodiment shown in FIG. 1.

In the final analysis, a system is thereby provided for administering a liquid medication, which has the following advantages:

By filling a medication reservoir 1 using a medication from a medication supply container 2 in filling device 3, it is ensured that the filling is performed properly. Filling device 3 ensures, in this context, that the right medication is filled in the correct quantity and having sufficient shelf life. Furthermore, filling device 3 is able to clean medication reservoir 1 as well as other components that are in touch with the medication. In addition, filling device 3 is able to cool medication supply container 2, and consequently it lessens external dependencies, such as on a refrigerator.

What is claimed is:

1. A system, comprising:
   a medication dosing apparatus;
   a reusable medication reservoir that is configured to hold a liquid medication, the medication reservoir being removable from the system;
   a medication supply container configured to hold a reserve of the liquid medication; and
   a filling device that automatically transfers the reserve of the liquid medication from the medication supply container to the medication reservoir;
   wherein:
      the medication dosing apparatus is fluidically connectable to, and disconnectable from, the medication reservoir; and
      at least one of:
         the filling device includes a cleansing device for the medication reservoir;
         the filling device includes a detecting device for an automatic detection of at least one of (i) the liquid medication being transferred from the medication supply container and (ii) a shelf life of the liquid medication being transferred from the medication supply container; and
         the medication reservoir is provided in a unit that is insertable into, and removable from the medication dosing apparatus, and that further includes an administration needle and a medication dosing device that (i) is configured to convey a dosage of the liquid medication to the administration needle, and (ii) is a conduit by which the reserve of the liquid medication is transferrable by the filling device to the medication reservoir.

2. A system, comprising:
   a medication dosing apparatus;
   a reusable medication reservoir that is configured to hold a liquid medication, the medication reservoir being removable from the system;
   a medication supply container configured to hold a reserve of the liquid medication; and a filling device that automatically ef transfers the reserve of the liquid medication from the medication supply container to the medication reservoir;

wherein:

the medication dosing apparatus is fluidically connectable to, and disconnectable from, the medication reservoir;

the medication reservoir is provided in a unit that is insertable into, and removable from, the medication dosing apparatus; and at least one of:

the filling device includes a cleansing device for the medication reservoir;

the filling device includes a detecting device for an automatic detection of at least one of (i) the liquid medication being transferred from the medication supply container and (ii) a shelf life of the liquid medication being transferred from the medication supply container; and the unit further includes an administration needle and a medication dosing device that (i) is configured to convey a dosage of the liquid medication to the administration needle, and (ii) is a conduit by which the reserve of the liquid medication is transferrable by the filling device to the medication reservoir.

3. A system, comprising:

a medication dosing apparatus;

a reusable medication reservoir that is configured to hold a liquid medication, the medication reservoir being removable from the system;

a medication supply container configured to hold a reserve of the liquid medication; and a filling device that automatically of transfers the reserve of the liquid medication from the medication supply container to the medication reservoir;

wherein:

the medication dosing apparatus is fluidically connectable to, and disconnectable from, the medication reservoir;

the medication reservoir is provided in a unit that is insertable into, and removable from, the medication dosing apparatus and that includes an administration needle and a medication dosing device; and at least one of:

the filling device includes a cleansing device for the medication reservoir;

the filling device includes a detecting device for an automatic detection of at least one of (i) the liquid medication being transferred from the medication supply container and (ii) a shelf life of the liquid medication being transferred from the medication supply container; and the medication dosing device (i) is configured to convey a dosage of the liquid medication to the administration needle, and (ii) is a conduit by which the reserve of the liquid medication is transferrable by the filling device to the medication reservoir.

4. The system of claim 2, wherein the removable unit is disposable.

5. The system of claim 1, wherein the filling device for automatically filling the medication reservoir is electrically operable.

6. The system of claim 1, wherein the filling device includes a cooling device for the medication supply container.

7. The system of claim 1, wherein the filling device includes the cleansing device for the medication reservoir.

8. The system of claim 7, wherein the cleansing device holds a cleansing agent.

9. The system of claim 1, wherein the filling device includes a liquid level monitor that monitors the medication reservoir.

10. The system of claim 2, wherein the filling device includes a device for at least one of a functional checking and a calibration of the removable unit.

11. The system of claim 1, wherein the filling device includes the detecting device for the automatic detection of the at least one of (i) the liquid medication being transferred from the medication supply container and (ii) the shelf life of the liquid medication being transferred from the medication supply container.

12. The system of claim 3, wherein the administration needle has at least one fluidic connection to the medication supply container when the removable unit is inserted into the filling device.

13. The system of claim 12, wherein one of the at least one fluidic connection is between the medication supply container and the removable unit.

14. The system of claim 1, wherein a pump, which has a fluidic connection to one of the administration needle and the medication reservoir, is provided for the automatic filling of the medication reservoir.

15. The system of claim 1, wherein the administration needle includes one microneedle or a plurality of microneedles.

16. The system of claim 1, wherein the medication dosing device is a micropump, whose drive is a part of the medication dosing apparatus and is not included in the removable unit.

17. The system of claim 3, wherein the medication dosing device (i) is configured to convey the dosage of the liquid medication to the administration needle, and (ii) is the conduit by which the reserve of the liquid medication is transferrable by the filling device to the medication reservoir.

* * * * *